United States Patent [19]

Weiner et al.

[11] Patent Number: 5,047,344

[45] Date of Patent: Sep. 10, 1991

[54] **INDUCTION OF SETTLEMENT AND METAMORPHOSIS IN *CRASSOSTREA VIRGINICA* BY MELANIN-SYNTHESIZING BACTERIA AND AMMONIA, AND METABOLIC PRODUCTS OF SAID BACTERIA**

[75] Inventors: Ronald M. Weiner, Rockville; Rita R. Colwell, Bethesda; Dale B. Bonar, Gambrills, all of Md.; Steven L. Coon, Falls Church, Va.; Marianne Walsh, Crofton, Md.

[73] Assignee: Research Corporation Techniques, Inc., Tucson, Ariz.

[21] Appl. No.: 185,647

[22] Filed: Apr. 25, 1988

Related U.S. Application Data

[63] Continuation-in-part of Ser. No. 567,023, Dec. 30, 1983.

[51] Int. Cl.[5] .......................... A01K 61/00; C12N 1/00; C12P 1/04; C12P 13/22
[52] U.S. Cl. .................................. 435/252.1; 424/93; 119/4
[58] Field of Search ............................ 424/93; 119/4; 435/252.1

[56] References Cited

U.S. PATENT DOCUMENTS 4,348,983  9/1982  Cooper ................................. 119/4
4,532,883  8/1985  Lockwood et al. ................... 119/4

OTHER PUBLICATIONS

Ivins et al., Inf. and Immunitiy, vol. 27, No. 3, Mar. 1980, pp. 721-729.

Primary Examiner—Howard E. Schain
Assistant Examiner—Choon Koh
Attorney, Agent, or Firm—Scully, Scott, Murphy & Presser

[57] ABSTRACT

The present invention relates to the discovery of a new bacteria of the genus Alteromonas which has been found to attract oyster larvae by the production of compounds involved in melanin synthesis. More specifically, the present invention contemplates a method for inducing the settlement and metamorphosis of *Crassostrea virginica* larvae by induction with certain metabolic substances produced by the present bacteria and its altered variants. Furthermore, the present invention is directed to other and derivative metabolic products which can be employed for their desired utility and application. In accordance with the present invention, it has been discovered that ammonia ($NH_3$) initiates settlement and metamorphosis of the oyster larvae in the same manner as the natural phenomena.

15 Claims, 7 Drawing Sheets

NORMAL ROD STRUCTURE

FORMING OF SLANTED INDENTATIONS
ACROSS THE CELL SURFACE

ADVANCED STAGE IN SPIRAL FORMATION

AN ELONGATED CELL WITH SPIRAL FORMS IN THE BACKGROUND

GENERAL VIEW OF ABERRANT VS.
NORMAL CELL MORPHOLOGIES

INDUCTION OF SETTLEMENT AND METAMORPHOSIS IN *CRASSOSTREA VIRGINICA* BY MELANIN-SYNTHESIZING BACTERIA AND AMMONIA, AND METABOLIC PRODUCTS OF SAID BACTERIA

This application is a continuation-in-part of U.S. Ser. No. 567,023, filed Dec. 30, 1983.

BACKGROUND OF THE INVENTION

The present invention relates to the discovery of a new bacterium which has been found to attract oyster larvae by the production of compounds involved in metabolism and melanin synthesis. More specifically, the present invention contemplates a method for inducing the settlement and metamorphosis of *Crassostrea virginica* larvae by induction with certain metabolic substances produced by the present bacterium and its mutagenically altered variants. Furthermore, the present invention is directed to other and derivative metabolic products which can be employed for their desired utility and application.

The formation of pioneer microbial communities on submerged surfaces appears to be beneficial to subsequent attachment and development of many invertebrate larvae. A number of investigations have established a general pattern of periphytic succession for colonization of clean surfaces immersed in seawater. In the initial phase after possible coating by organic matter, bacteria attach to such a surface and begin to grow, forming microcolonies within several hours. Subsequently, diatoms, fungi, protozoans, micro-algae and other microorganisms attach to the surface, forming what has been termed the primary slime layer. This primary microbial colonization appears to be a prerequisite for the final stage of succession in which microorganisms, viz., invertebrates, attach and grow on the surface. Although most surfaces are eventually colonized, the rapidity and extent of the process depends on the nature of the surface material, the prevailing environmental conditions and the composition of the periphytic populations.

Two invertebrate species for which some information has been ascertained concerning the effect of the periphytic organisms on their induced metamorphosis are the sea urchin, *Lytechinus pictus*, and the hydroid, *Hydractinina echinata*. It has been determined that for Lytechinus, the responsible factor is a low molecular weight bacterial by-product, probably proteinaceous having a molecular weight less than 5000 daltons. It has also been found that planulae larvae of Hydractinia metamorphose in response to a product emitted by certain marine, gram-negative bacteria at the end of their exponential growth phase. If these bacterial cultures are subjected to osmotic shock, the activity shows up in the supernatant, suggesting that the critical product is a soluble factor rather than a bound one. When Hydractinia are kept in sterile conditions, they do not metamorphose.

In a series of experiments designed to determine the physiological mechanism by which the stimulus activates metamorphosis, it has been demonstrated that the inducer may operate by stimulating the $Na^+/K$-ATPase of larval cell membranes. Such findings are the first real steps toward understanding how larvae can mount a broad spectrum morphogenetic response to specific environmental stimulation. Moreover, recent reports have shown that Vibrio sp. excretes a product that induces metamorphosis of the cnidarian, *Cassiopea andromeda*. Other investigations demonstrate that larvae of the marine annelid, *Janua brasiliensis*, settle on certain microbial films and that certain specific bacteria may induce metamorphosis. These observations suggest that the processes are mediated by larval lectins binding to extracellular polysaccharides or glycoproteins, produced by the bacteria.

In both the natural environment and in oyster mariculture operations, the setting process, whereby planktonic oyster larvae alight on an oyster shell or plastic sheet and undergo metamorphosis to form attached oyster spat, is crucial to successful oyster development. It is also known that the larvae of *Ostrea edulis*, the European oyster, prefer setting on surfaces covered with a film of bacteria and diatoms. Natural periphytic microbial populations are, therefore, significant in successful oyster setting. The same situation is likely to be true of oyster mariculture, since a rich source of bacterial flora has been associated with oyster larvae and larval food sources in hatcheries. In some cases, bacteria have also been implicated in the death of oyster larvae. Since the presence of microorganisms significantly affects oyster development, improved knowledge of the biology of these microorganisms and particularly an understanding of their beneficial and/or deleterious effects on developing oysters, will further improve oyster setting and development in both natural and artificial settings.

Oyster larvae display three characteristic patterns toward organic compounds and microorganisms, i.e., positive, inactive and negative chemotaxis. In one particular study, a marine pseudomonad was attractive to larvae while a marine yeast elicited no response. It has also been suggested that an alga, Isochrysis, may produce extracellular oyster attractant. Conversely, it is known that oyster larvae do not set preferentially on surfaces to which a marine isolate, *Hyphomonas neptunium*, is affixed. It is believed that *H. neptunium* does not antagonize settlement, but rather that it competitively establishes itself on surfaces and excludes bacterial species which would be beneficial to oyster settlement.

The question, however, of which of the periphytic microorganisms and which of their products specifically attract or promote the setting and subsequent development of oyster larvae has not been answered heretofore. Free swimming larvae, shortly after spawning, seek a suitable place to settle and attach themselves. A number of environmental conditions are involved in settlement, salinity and nutritional availability are probably the most important. But once larvae are satisfied with these initial conditions, they appear to respond to a biochemical cue to settle and attach themselves. That biochemical cue is released by a pigmented bacterium which adheres strongly to surfaces such as oyster shells and which is the subject of this invention.

SUMMARY OF THE INVENTION

It is, therefore, one object of the present invention to provide marine bacteria which are capable of inducing the settlement and metamorphosis of *Crassostrea virginica* larvae.

Another object of this invention is to provide a method for inducing the settlement and metamorphosis of *Crassostrea virginica* larvae.

A further object of the present invention is to isolate and purify the metabolic products of the present bacteria and those of its altered variants.

Still another object of this invention is to employ the isolated metabolic products of the present bacteria for their desired utility.

These and other objects are achieved, in the first instance, by the discovery of a melanin-synthesizing marine bacterium, designated LST (LST-W), which has been mutagenically altered in accordance with this invention to provide two particular variants thereof, designated DIF (LST-D) and HYP (LST-H). A spontaneous variant, designated VIS (LST-V) has also been discovered. These bacteria have been taxonomically identified as a new species of the genus Alteromonas, a genus established to include a diverse array of polarly flagellated, aerobic marine bacteria. These bacteria have been named and characterized as *Alteromonas colwelliana*. Each bacterium has been deposited with the American Type Culture Collection (ATCC). LST-W has been accorded the accession number 39565;LST-D has been accorded the accession number 33887;LST-H has been accorded the accession number 33888; and LST-V has been accorded the accession number 53761. LST and its variants, DIF, HYP and VIS and/or any of their variants, can be employed in a process for inducing the settlement and metamorphosis of *Crassostrea virginica* larvae. In fact, it has been discovered that all of the members of the genus Alteromonas which have the characteristics contemplated by the present invention including, particularly, the ability to produce the various critical metabolic products elucideated hereinafter, also have the ability to induce the settlement and metamorphosis of *Crassostrea virqinica* larvae, i.e., such capability is attributable to the production of said metabolic products. This process may be employed in a natural or artificial environment, e.g., a mariculture operation, to induce the setting process of oyster larvae during which process the larvae alight on clutch or other suitable surface materials, and undergo metamorphosis to form attached oyster spat. The present method can be effected by exposing the *Crassostrea virginica* larvae to the bacteria of the genus Alteromonas including, for example, LST, DIF, HYP and VIS in an aqueous environment. Moreover, it has been found, in accordance with the present invention, that settlement and metamorphosis is initiated by the metabolic products produced by this genus of bacteria, specifically, a low molecular product (~350 daltons) of tyrosinase activity which includes the product L-DOPA which itself has been found to initiate oyster settlement and metamorphosis, and which also includes DOPA mimetics, for example, trihydroxyphenylalanine, and the class of catecholamines, for example, epinephrine and norepinephrine.

In the context of this invention, it has also been discovered that ammonia ($NH_3$) also induces the settlement and metamorphosis of oyster larvae in a similar manner to naturally induced behavior.

Furthermore, it has also been discovered that Alteromonas produce an additional exopolymer, characterized as a polysaccharide adhesive viscous exopolymer (PAVE) which is useful, e.g., as an adhesive, a marine glue and as an oyster setting surface. The metabolic products of the present bacteria enumerated above including, particularly, the low molecular weight (~350 daltons) product of tyrosinase activity can be isolated and employed for their desired utility, e.g., chemical cues. The exopolymers can be purified and used as adhesives and oyster setting surfaces. The DIF, HYP and VIS variants exhibit particularly heightened levels of production of these metabolic substances.

DETAILED DESCRIPTION OF THE INVENTION

Figure 1:
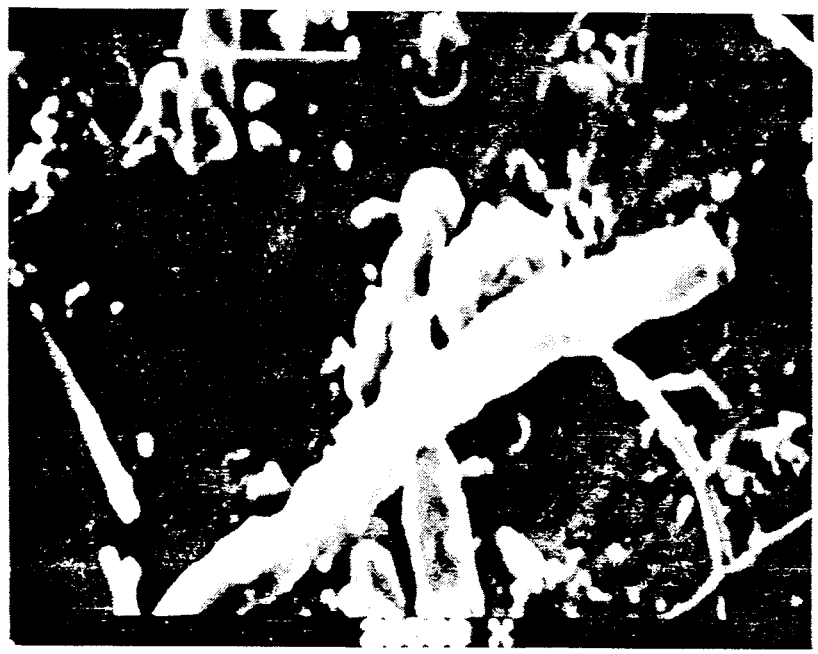
FIG. 1 is a scanning electron micrograph (10,000 x) of a normal rod structure.

In accordance with the present invention, new melanin-synthesizing marine bacteria of the genus Alteromonas, including species designated LST-W, LST-D, LST-H and LST-V, have been isolated in continuous and close association with oysters and can be employed in a process for inducing the settlement and metamorphosis of *Crassostrea virginica* larvae. It has also been found in accordance with this invention that ammonia ($NH_3$) induces settlement behavior and subsequent metamorphosis of oyster larvae in a similar manner as the natural phenomenon and under the same conditions. Moreover, several metabolic products have been recovered from the present bacteria which are highly desirable for their industrial, experimental or medical utility.

Thus, among the many advantages of the present invention, it has been surprisingly discovered that the novel marine bacteria of this invention, *A. colwelliana*, and, particularly, the mutagenically altered variants thereof, designated DIF and HYP, including the spontaneous variant VIS, which have also been accorded the ATCC accession numbers 39565, 33887, 33888 and 53761, respectively, are capable of specifically inducing the setting and metamorphosis of *Crassostrea virginica* larvae by the production of certain metabolic products associated with (metabolism and exopolymer e.g., melanin, and polysaccharide synthesis. Moreover, it has been discovered that the various species of Alteromonoas, e.g., *A. macleodii* (ATCC No. 27126) and *A. nigrifaciens* (ATCC No. 23327) all synthesize polysaccharide exopolymers (PAVE) which may be employed as setting films or as adhesives. The aforementioned metabolic products include, for example, melanin, pheomelanin, dihydroxyphenylalanine ("DOPA" or "L-DOPA"), and polysaccharide viscous exopolymers (PAVE) have been found to have significant commercial, experimental and medical utility.

In more detail, LST and its related variants are variants are representative members of the Alteromonas genus, aerobic, highly motile, gram-negative rods, with a guanosine to cytosine ratio of 45.6% and have been found to attract oyster larvae by production of $NH_3$, DOPA/DOPA mimetics including trihydroxyphenylalanine and polysaccharide exopolymers. The exopolymers are most abundantly synthesized during the late stationary-decline phase of bacterial growth when the adenylate energy charge is 0.72 and the organism is undergoing morphological transition to the elongated helical form. The particularly active agent in this respect is a low molecular weight product (less than about 350 daltons) of tyrosinase activity and includes the product L-DOPA which itself has been found also to initiate oyster settlement and metamorphosis, and mimetics of L-DOPA including, for example, trihydroxyphenylalanine and including catecholamines. The bacteria grow optimally in 35 ppt salt, and within a range of 15-75 ppt at 25° C. and do not produce spores. The bacteria readily attach to a variety of surfaces including, preferentially, glass and oyster shells, and also to plastic, aluminum, and the like. The biochemical characteristics of LST are set forth in Table 1 below. These bacteria have been named and characterized as *Alteromonas colwelliana*.

LST, DIF, HYP/and VIS, though heterotrophic, have relatively simple nutritional requirements as set forth below in Table 2. Although serine and methionine alone do not support the growth of LST or its related variants, aspartic and glutamic acids, in combination with serine, methionine or each other, do sustain the organism. Therefore, either aspartic or glutamic acid could serve as a carbon and energy source. In practice, however, it is preferred that a growth medium of aspartic acid and a solution of inorganic salts be supplemented with glutamic acid to remedy the growth-limiting effects which may be observed after numerous subculturings.

LST and its variants, particularly DIF, HYP and VIS, are marine bacteria that use amino acids, but do not use carbohydrates, fail to ferment sucrose, mannose or arabinose (see Table 1), and fail to grow in a medium containing 1% glucose and salts solution.

In the stationary phase of growth, these bacteria routinely produce a reddish-brown pigment, which has been identified as a melanin and which bio-synthetic pathway has been discovered to mediate the interaction between the bacteria and the oyster larvae. As aforesaid, the particular biosynthetic product which initiates settlement and sustains metamorphosis is a low molecular weight product (less than about 350 daltons) of tyrosinase which includes L-DOPA/L-DOPA mimetics. Notably, oyster larvae must settle prior to metamorphosis and do so in response to a chemical cue, i.e., a positive chemotaxis. In this regard, it has been determined that the melanin macro molecule described above is actually a heteropolymer of a number of different monomeric precursors. Of particular importance is dihydroxyphenylalanine (L-DOPA), a melanin precursor which increases oyster larval search behavior, and ultimately oyster spat attachment, and thus supports the settling of larvae which has been found to induce settlement and metamorphosis itself L-DOPA is also known to have significant physiological applications, primarily acting as a neurotransmitter precursor in humans and animals and is often used in the treatment of Parkinson's disease or other related nervous disorders.

Thus, in one aspect of the present invention, two mutagenically altered variants of the parent LST bacterium, designated DIF and HYP, have been isolated through conventional techniques such as, for example, mutagenesis with ethyl methane sulfonate (EMS) or ICR 191 (Institute of Cancer Research intercalating agent).[The bacterium VIS is a spontaneous mutant which also possesses the heightened activity of DIF and HYP. Each of these variants exhibit unique characteristics relative to the production of the metabolic pigment products, e.g., melanin, pheomelanin, DOPA, tyrosine, tyrosinase and related enzymes. Each of the variants can therefore be selectively employed in a process for the settlement and metamorphosis of oyster larvae. By the term variant or mutant is meant the genetic derivative of the parent bacterium which is obtained by single or multiple base substitutions, deletions, insertions or inversions whether spontaneously or artificially induced.

Furthermore, the LST, DIF, HYP and VIS trains among the various species of Alteromonas, including, for example, *A. macleodii* (ATCC No. 27126) and A. nigrifaciens (ATCC No. 23327), each produce an additional exopolymer as a product of their metabolism. This product, characterized as a polysaccharide adhesive viscous exopolymer (PAVE), is associated with nine major proteins that enhance adhesiveness and which play an integral part of that property. One constituent of PAVE having particular adhesive enhancement quality is the aforementioned low molecular weight product of tyrosinase metabolism which has been detected absorbed to PAVE and possibly ionically bound to it. This acid polysaccharide has been found to have excellent utility as a marine cement or glue, a water-proofing material and an emulsifying agent which can be employed, for example, in the clean-up and removal of oil and organic spills.

In one particular embodiment of this invention, each of the bacteria of the genus Alteromonas can be employed in a process for inducing the settlement and metamorphosis of *Crassostrea virginica* larvae. Accordingly, the bacteria are cultured in a growth medium and provided with a suitable surface material to which they can affix due to the production of the acid polysaccharide exopolymer. Oyster larvae are simultaneously or thereafter exposed to the bacteria or, alternatively, to their metabolic products or the metabolic, low molecular product of tyrosinase including melanin, pheomelanin, L-DOPA, NH , or mixtures thereof for a time and under conditions to effect larvae setting. Once settlement occurs, i.e., foot extension of the larvae, crawling behavior, search behavior and cementation, metamorphosis, i.e., maturation of the oyster larvae, naturally progresses in response to the biofilms and micro-colonies of bacteria which develop on the provided surface material.

By way of explanation, although not wishing to be bound, it is believed that when sufficient numbers of bacteria are achieved, during the decline phase of growth, the bacterial colonies produce a high concentration of tyrosinase synthesizing DOPA, including the DOPA mimetics, e.g., trihydroxyphenylalanine, which attract oyster larvae. The larvae appear to be able- to "ingest" (feed upon) these elongated cells ($\geq 5$ um) of bacteria which are observed to occur during that stage of growth. Moreover, an oyster product appears to provide nutrients for LST reproduction. Evidence indicates that oyster larvae respond to multiple cues from *A. colwelliana* formed films. Settlement and search behavior is induced by the aforesaid soluble metabolic products which also include ammonia. These compounds may be released into the environment or may be sequestered and concentrated within the films. Although cementation and metamorphosis of the larvae proceed from the initial cue, these processes are apparently heightened by the presence of the insoluble polysaccharide exopolymers secreted by *A. colwelliana* on surfaces of attachment. In marine broth, for example, a minimum of 24 hours is necessary for film formation to be inductive to oyster larvae and two to three day old films show heightened induction.

The preferred growth medium for the bacteria of this invention is brain heart infusion with about 3% NaCl, although other conventional growth media which meet the nutritional requirements set forth above will suffice. (Alternative media are set forth in the Examples under Organism and Culture Conditions.) It is also preferable that the oyster larvae be fed *Isochrysis galbana* and *Monochrysis lutheri* at a rate of about $2 \times 10^5$ cells/ml of culture per day. The ideal surface upon which the bacteria can be grown is clutch, although glass and plastics coated with Alteromonas films are also effective and more commercially expedient. Materials such as plastics or aluminum are also satisfactory.

Since the LST strain is mutagenically altered in accordance with this invention using ICR 191 to obtain the DIF and HYP variants, each variant has its own unique characteristics. Specifically, the DIF bacterium, ATCC number 33887, produces a low molecular weight pigment ($\leq 30,000$ daltons) that readily diffuses into the water column, i.e., any body of water. It is preferable, therefore, that this bacterium is employed in a process to induce high proportions of oyster larvae to uniformly set on varying surfaces to promote enhanced, but undirected, set. Moreover, the DIF strain specifically produces increased amounts of pheomelanin. On the other hand, the HYP bacterium, ATCC number 33888, produces amplified amounts of melanin and melanin precursors of high molecular weight ($\geq 100,000$ daltons) that do not readily diffuse into the water column. It is preferable that the HYP variant is employed in a method to induce setting on specific surfaces for high level production of oyster development, and for the recovery of higher amounts of the melanin and melanin precursor metabolic products such as, for example, melanin, DOPA, tyrosine, tyrosinase and related enzymes.

Notably, LST-V synthesizes increased amounts of PAVE and, in particular, considerably more than the LST-W on the synthetic media. Each of the bacterial strains produce high amounts of the exopolymer, an acid polysaccharide, which can be employed, for example, as a marine cement, a water-proofing substance and/or as an emulsifying agent.

In a further embodiment of this invention, the acid polysaccharide exopolymer (PAVE) which is metabolically produced by the present bacteria is isolated together or apart from its nine associated proteins, for example, by solubilizing the polysaccharide in an acetone-alcohol or isopropanol solution. The exopolymer can be precipitated at water-solvent interface.

In another embodiment of this invention, it has been discovered that ammonia ($NH_3$) induces settlement behavior and subsequent metamorphosis of oyster larvae, *Crassostrea virginica*. Since ammonia ($NH_3$), and not the ammonium ion ($NH_4+$), is the inducing molecule, the response of the larvae to an ammonia solution (or even the bacteria supernatant) is pH sensitive. For example, at a pH of 8.0 (the pH or normal sea water), the threshold concentration of total ammonia/ammonium is about $2 \times 10^{-3}M$ with a maximum response attained at about $8 \times 10^{-3}M$. Higher concentrations are required at lower pH. The concentration of ammonia gas ($NH_3$) is a function of both total ammonia concentration ($NH_4^+ + NH_3$) and pH. The relationship is described by the formulas:

$$\frac{[NH_4^+]}{[NH_3]} = (1.8 \times 10^{-5}) \log^{-1}(14 - pH) = r \qquad a)$$

$$(r+1)[NH_3] = [NH_4^+ + NH_3] \qquad b)$$

E.g., at pH 8.0, $r = 18.0$ (equation a). Then, for a total ammonia concentration of $2 \times 10^{-2}M$ at pH 8.0, $$[NH_3] = \frac{2 \times 10^{-2}}{(18.0 + 1)} = 1.05 \times 10^{-3} M.$$

At a total ammonia/ammonium concentration of $8 \times 10^{-3}M$ (pH=8.0), a maximal larval settlement response is attained within about ten minutes.

Accordingly, the present invention contemplates a method for inducing the settlement and metamorphosis of oyster larvae, *Crassostrea virginica*, by exposing the oyster larvae to ammonia ($NH_3$) in solution having a concentration of at least about $2 \times 10^{-3}M$ (ammonia/ammonium), but no higher than $2 \times 10^{-2}M$ at pH 8.0. In the same manner as that described above for inducing settlement by natural behavior (*Alteromonas colwelliana*), the larvae are provided with a suitable surface upon which to affix. Once settlement occurs, metamorphosis, i.e., maturation, naturally progresses in response to the $NH_3$.

As aforesaid, actual attachment and metamorphosis can be augmented by the presence of PAVE on the surface. For a better understanding of the present invention with other and further objects, reference is made to the following experimental descriptions and examples.

EXAMPLE I

MATERIALS AND METHODS

Organism and Culture Conditions

LST was isolated on Marine Agar (Difco 2216) slants. Cultures were grown in a gyratory water bath (New Brunswick Scientific Model G76), at a setting yielding 8.5 ppm dissolved oxygen, at 25° C. The media employed were Marine Broth (Difco 2216), AGMS Synthetic Medium and AG Synthetic Medium, formulated similarly to the AGMS but lacking methionine and serine. The exact composition of AGMS and AG broths is set forth below. Solid synthetic media were prepared by adding 1.5% Agar (Difco). LST did not grow on TCBS.

| COMPOSITION OF THE AGMS AND AG SYNTHETIC MEDIA |
|---|
| The AGMS Synthetic Medium consists of two stock solutions: |
| Stock #1: |

-continued

COMPOSITION OF THE AGMS AND AG SYNTHETIC MEDIA

| | |
|---|---|
| NaCl | 19.45 g/L |
| $Mg.Cl_2.6H_2O$ | 8.80 g/L |
| $Na_2SO_4$ | 3.14 g/L |
| $CaCl_2$ (anhydrous) | 1.80 g/L |
| KCl | 0.55 g/L |
| $NaHCO_3$ | 0.16 g/L |
| KBr | 0.08 g/L |
| $H_3BO_3$ | 0.022 g/L |
| $SrCl_2$ | 0.034 g/L |
| $NaSiO_3$ | 0.004 g/L |
| $NH_4NO_3$ | 0.0016 g/L |
| $Na_2HPO_4$ | 0.008 g/L |
| Ferric Ammonium Citrate | 0.10 g/L |

The salts solution is autoclaved at 121° C. for 15 min at 15 lbs pressure. Sterile solution was stirred to evenly distribute the precipitate formed.
Stock #2:

| | |
|---|---|
| Aspartic Acid | 23.77 g/L |
| Glutamic Acid | 26.27 g/L |
| Methionine | 0.39 g/L |
| Serine | 17.16 g/L |

The pH of the Stock #2 solution was adjusted to 7.2-7.4 using 6N NaOH. Sterilization by autoclaving as above followed pH adjustment.
AGMS Medium consists of a mixture of 30 ml Stock #1 with 70 ml Stock #2.
AG medium uses the amino acid pool given below:
Stock #3:

| | |
|---|---|
| Aspartic Acid | 26.27 g/L |
| Glutamic Acid | 23.77 g/L |

Stock #1 and Stock #3 were mixed in the same proportions as for AGMS Medium (30-70) after adjusting the pH of the solution to 7.6 with 6N NaOH and sterilizing the solution.
Stock #4: Phosphate Solution

| | |
|---|---|
| $K_2HPO_4$ | 13.6 g/L |
| $K_2HPO_4$ | 21.3 g/L |

Autoclave separately, add 0.46 ml/100 ml GAMS.

Synthetic Medium Development and Growth Curves

The AGMS Synthetic Broth sustained the growth of LST when supplemented with 2% NaCl (NaCl final concentration 3%). Using a drop-out series experiment, the contribution of each amino acid supplied in AGMS (aspartic acid, glutamic acid, methionine and serine) to the growth of LST was evaluated by direct microscopic counts (phase contrast 0.19 μm resolution) and by viable counts.

To approximate the growth rate of LST, turbidimetric measurements of cultures grown in Marine and AG broths were made over a period of 470 hrs using a Klett-Summerson Photoelectric Colorimeter with a green filter.

Morpholoqy

Cell morphology during the growth cycle of LST was monitored under phase contrast microscopy (Series 10 AO Microscope 0.19 μm resolution). Scanning electron microscopy was used for a more detailed view of the structure of normal and aberrant LST cells. Bacterial cells were fixed according to a procedure described by Belas and Colwell (1982). To minimize the amount of inorganic precipitate, LST cells were grown for 48-96 hrs in AG Broth. The cultures were then centrifuged (Model PR-G IEC Refrigerated Centrifuge) at 2500×g for 10 min decanted, resuspended in 10 ml PBS and washed twice. After the final centrifugation, the pellets were resuspended in 10 ml PBS and 1 ml of 25% glutaraldehyde (Polysciences) was added. The mixtures were allowed to fix for 1 hr either at room temperature or overnight at 4° C. Following fixation, the bacterial suspension was passed through a 13 mm Swinex holder with a 0.2 μm Nucleopore filter, using a syringe attached to the Swinex. The volume that passed through each filter varied between 1 and 5 ml of culture suspension; care was taken to avoid damaging both fragile cell appendages and the filter. The syringe was then refilled with 5 ml of 0.2M cacodylate buffer with 2.5% glutaraldehyde; half the mixture was pushed through the filter, and the Swinex holder was sealed and stored overnight at 4° C. After fixation, dehydration was accomplished in seven steps, in which 5 ml EtOH (sequential concentrations of 30, 50, 70, 90 and 3×100%) were slowly passed through the filter over a period of 30-60 minutes.

Specimens were further prepared for microscopy as follows: The filters were critical point dried and placed cell side up on SEM stubs using double stick adhesives. To reduce charging of the specimen, small drops of silver paint were placed on four corners of the stub connecting the filter surface to the stub metal. The stubs were coated with Ag/Pd metal alloy in a sputter coater, and then stored for scanning electron microscopy in a desiccated environment.

To determine the presence and location of flagella on LST, the procedure of Mayfield and Innis (1977), a modification of Gray's stain, was used on wet mounts of motile bacteria. Stained cells were examined with phase contrast microscopy.

Figure 2:
FIG. 2 is a scanning electron micrograph (20,000 x) illustrating the formation of slanted indentations across the cell surface of the LST bacterium.

As anticipated, LST incurred a lengthy lag period (27 hrs) when transferred from Marine to AG medium. This lag period was not observed when cultures were transferred from AG to AG medium (FIG. 2). The generation time of LST at 25° C. was 4 hrs in marine broth and 7 hrs in AG Medium. The slower growth rate in the Synthetic Medium is presumably correlated to the availability of nutrients in the two media. All growth factors must have been synthesized de novo from glutamic and aspartic acids in AG, whereas Marine Broth was replete with numerous vitamins from Yeast extract and a wide variety of nutrients in peptone.

Mutagenesis

Ethyl Methane Sulfonate

To test the hypothesis that LST pigment attracts spat, pigment-less variants were desirable controls. Consequently, LST was mutagenized with ethane methane sulfonate (EMS; Sigma) according to a modification of the procedure used by McCardell (1979). Logarithmically growing cultures of LST were suspended in 0.066M PBS to an approximate concentration of $2 \times 10^9$ cells/ml. EMS was added to 1 ml aliquots of culture to yield final concentrations ranging between 10-30 ul/ml (5 ul intervals). The resulting suspensions were incubated for 1 and 1.5 hrs in a G76 Water Bath Shaker (New Brunswick Scientific) at setting 5. The suspensions were diluted 1:10 in PBS, centrifuged, washed with 5 ml PBS and resuspended in 3 ml PBS. Two ml of the final suspension were inoculated in AG Broth and incubated 2-5 days. After this adaptation period, the mutagenized and recovered culture was then spread on Marine Agar. The remaining 1 ml of treated suspension was used to "spread plate" directly on AG and Marine agars. Screening of mutants was assessed visually, since pigment production was easily scored on agar plates.

Mutagenesis with EMS for 1 hr reduced the viability of LST 2-3 logs as determined by spread plate counts on Marine Agar (Table 6). No colonies formed on AG Agar when LST was "plated" directly after mutagenesis. This result was not unexpected: Since the minimal medium lacks so many growth factors, auxotrophic mutations would be conditionally lethal. Mutagenized suspensions, after 2-5 days "holding" periods in AG Broth, were streaked on Marine and AG agars. Spread plate counts on Marine Agar ranged from $1.3-6.6 \times 10^9$, while they were approximately two logs lower on AG Agar: $1.4-6.5 \times 10^7$ (Table 6). The colonies on AG Agar were probably in part progeny of cells that remained in stasis in the AG Medium, repairing damage to the chromosome and possibly even back mutating.

Suspensions treated with EMS (all concentrations) for 1.5 hrs did not yield any colonies either after direct plating (Marine or AG agars), or after the holding period in AG Broth.

No pigment-less mutants were detected among the approximately 5000 colonies screened, on either undefined or minimal media. A number of factors may have led to this failure. Two of the possibilities, not mutually exclusive, are that pigment production is part of an obligate cell survival pathway, a serious consideration since melanin is part of the tyrosinase metabolism. In this case, obtaining pigment-less variants may prove an unrealistic goal. A second possibility is based on reports that pigment synthesis is essentially dependent upon a single enzyme, tyrosinase or a tyrosinase-like derivative. In this instance, mutations involving the mel gene would appear with very low frequencies. Furthermore, the likelihood of another mutational aberration that would be lethal to cells containing a lesion in a mel gene would be high. In any case, we had only screened about 5000 colonies by this procedure, and a mutation rate of less than 0.02% is not uncommon. Mutagenesis experiments using ICR 191 were designed with a holding period in Marine Broth rather than AG Broth to minimize auxotrophic lethality.

ICR 191

The procedures were modified slightly from those described above. The reaction mixture consisted of AG minimal medium containing 10% Marine Broth, $3-6 \times 10^8$ LST/ml and 10 ug ICR 191/ml. Cells were incubated at 30° C. in the reaction mixture for 12 hrs and then diluted 1:100 into fresh Marine Broth to provide an adaption period of between 12-72 hrs. Mutants were screened on Marine, AG and AGT agars.

A total of 24,803 colonies were screened. Thirty-nine colonies varied in pigmentation, seven had no pigment (hypo), two were darker (hyper), includingg the HYP variant, two were light tan, 27 were various shades of red from which the DIF variant was isolated and one was yellow. The paucity of pigment mutations suggested that either only a single enzyme was necessary for pigmentation (or any one of two or more enzymes) or that somehow pigmentation was somehow linked to viability. The first of these two hypotheses is consistent with the pigment being a melanin. These results also suggest that LST may produce more than one pigment, the lighter ones being masked by the brown ones. Also interesting, the seven mel- or hypo "mutations" have not been stable, reverting on average about one in 3-10 generations.

About 83% of the colonies that grew in Marine Agar, grew on AG Agar revealing that a considerable fraction of auxotrophic mutations were produced. Inexplicably, only 66% of the colonies that grew on Marine Agar, grew on AGT Agar.

Pigment Isolation and Characterization

Crude pigment was obtained from broth cultures that had been grown for at least 48-72 hrs (to stationary phase) in either Marine or AG broths. Spent medium was centrifuged at $2500 \times g$ for 15 min to remove the cells. The supernatants were dialyzed against distilled water for 24 hrs and pigment was purified by gel filtration.

Sephadex G-50, G-75 and G-150 columns (Pharmacia Chemicals), in which the dextran beads were swollen in distilled water in 0.02% sodium azide to prevent microbial growth, were calibrated with lysozyme, tripsinogen, egg albumin, bovine albumin and yeast alcohol dehydrogenase standards obtained from Pharmacia. Running buffer consisted of distilled water with 0.02% sodium azide, adjusted to pH 8.5. Void volume was determined using blue dextran 2000. The fractions were monitored at 280 nm.

The pigment fractionation was carried out on an Isco Model 328 Fraction Collector, using an ISCO Type 6 Optical Unit and an ISCO Model UA-5 Absorbance/Fluorescence Monitor to identify the pigment fractions.

The optical densities of the Sephadex fractions were analyzed using a Model 25 Beckman Spectrophotometer in the scan mode (200 through 750 nm). In general, melanin had a much lower extinction coeffecient in the visible range than in the ultraviolet, making dilutions of the samples necessary for analysis in the range of 200-350 nm. The absorption spectra of glutaraldehyde-treated cultures were also determined. Using a second basic method of extraction, crystallized pigment was obtained by a procedure in which the liquid phase of a culture supernatant was boiled off and the "residue" was dried at 90° C.

Another experiment was designed to determine whether a significant amount of pigment was cell-associated, or whether most of the pigment was excreted. Cell pellets ($2500 \times g$, 15 min) were resuspended in phosphate buffered saline (PBS), sonicated at low speed (setting 30) for 30 seconds (Bronwill Biosonk IV Sonicator) and recentrifuged. This pigment preparation was compared spectrophotometrically to a culture, containing both cells and soluble pigment, treated in the same way with sonication. Standard solutions of melanin (Sigma) at a concentration of 0.25 mg/ml distilled $H_2O$ and L-DOPA (Sigma) at a concentration 1.0 mg/ml were compared with the absorbance spectra of LST culture pigments.

Pigment solubilities were preliminarily tested, using 0.5 ml culture supernatant to 2.5 ml solvents. The solutions were agitated and maintained for at least 30 min after which they were centrifuged to separate potential precipitates. The criteria of Zussman, et al. (1960) were adopted to describe the solubility of pigment in the solvents. Pigments were designated "soluble" if they dissolved in the solvent, "slightly soluble" if the solvent became colored but the pigment did not dissolve, and "insoluble" if no color was imparted to the solvent. Solvent-pigment combinations were also examined by spectrophotometer.

Infrared (IR) spectra were determined (Perkin Elmer 281 IR spectrophotometer). Experimental samples were column purified, dialyzed, freeze dried LST pigment from culture supernatant to which one drop of paraffin oil was added. Commercially obtained melanin (Sigma), synthesized via the photooxidation of L-DOPA, was used as a control.

After LST cultures reached stationary phase, a soluble pigment, ranging in color from reddish-brown to dark brown, became evident. It was retained in dialysis and was precipitated by acidified water, ethanol and methanol (Table 4). The pigment was relatively soluble in water, only slightly soluble in ethanol and methanol and insoluble in acetone, chloroform, cyclohexane and ethylene dichloride.

Figure 3:
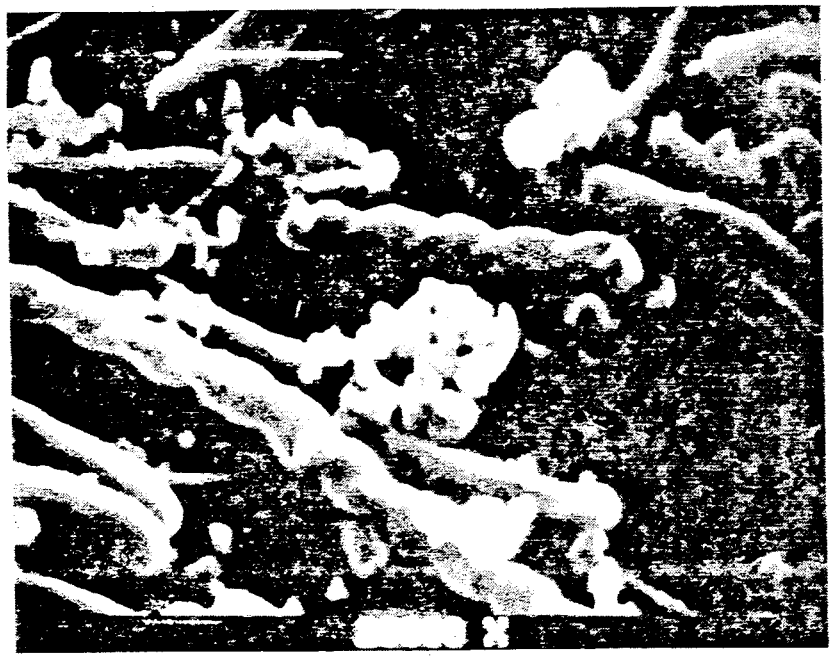
FIG. 3 is a scanning electron micrograph (20,000 x) illustrating the advanced stage of spiral formation of the LST bacterium.

The crude pigment exhibited three maximum absorbance intervals at 260, 407 and the largest at 220 nm (Table 5, FIG. 3). Glutaraldehyde partially oxidized the pigment, shifting the absorbance peaks to 233, 273 and 435 nm. When the pigment was totally oxidized, it appeared darkest and an absorbance peak was shifted still further from 273 to 293 nm. Additionally, there was generalized absorption in the visible region.

Figure 4:
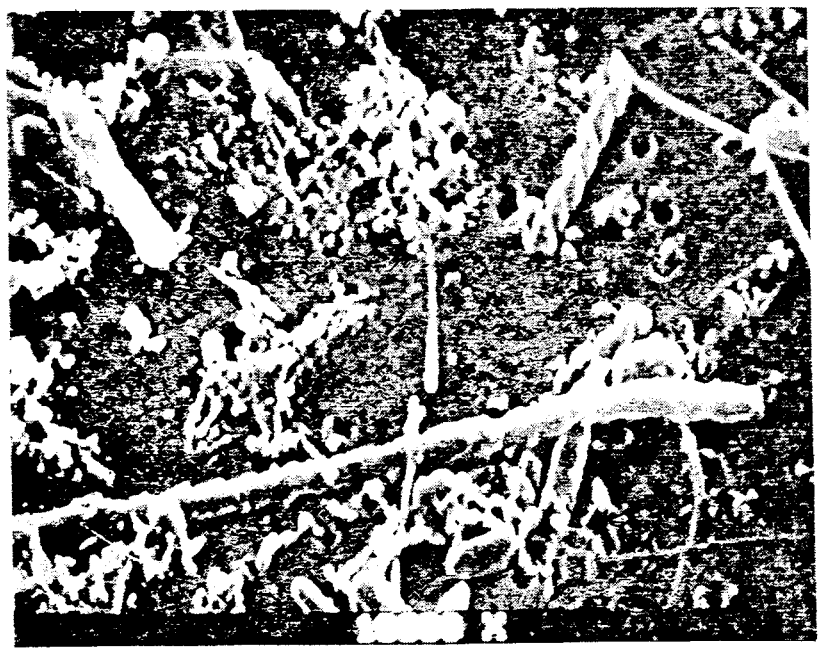
FIG. 4 is a scanning electron micrograph (10,000 x) illustrating an elongated cell of the LST bacterium with spiral forms shown in the background.
Figure 5:
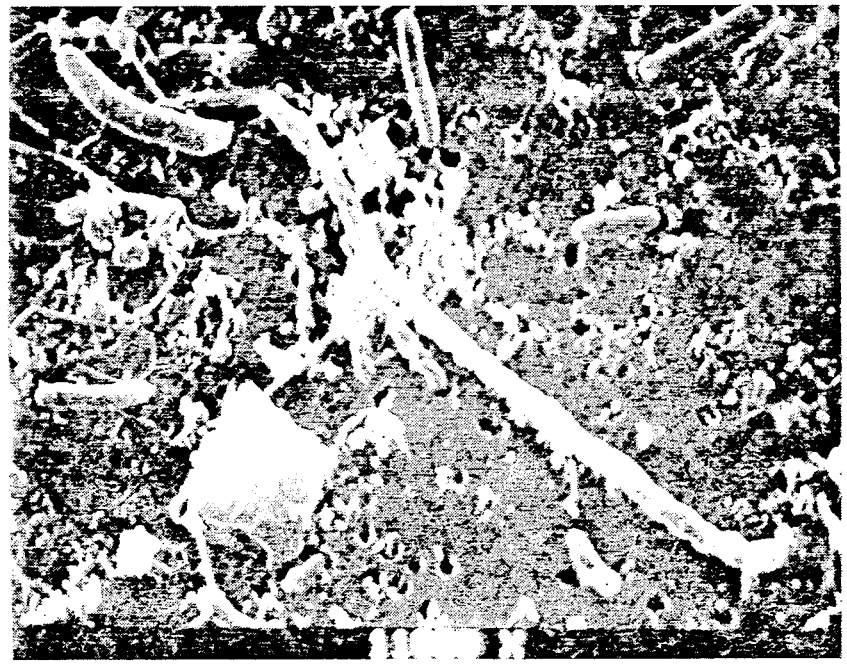
FIG. 5 is a scanning electron micrograph (11,000 x) illustrating a general view of aberrant and normal cell morphologies of the LST bacterium.
Figure 6:
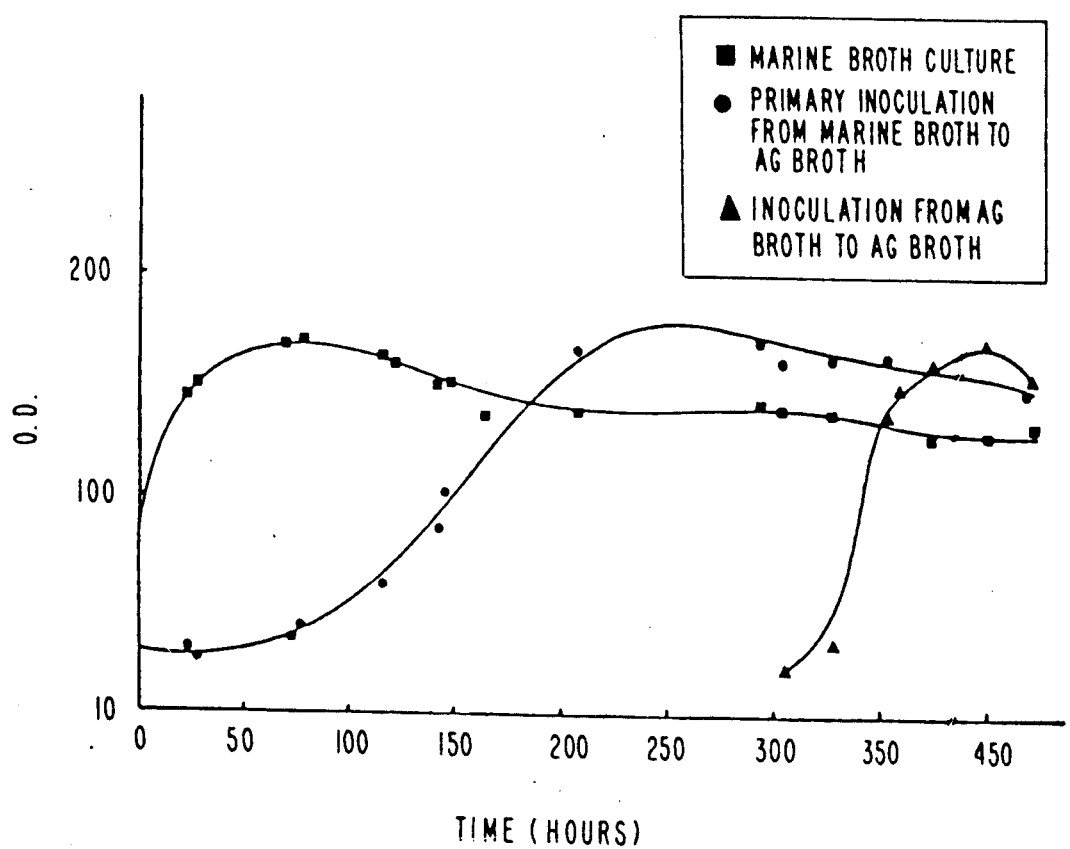
FIG. 6 is a graphic illustration depicting growth curves of LST cultures grown in Marine and AG synthetic broths.
Figure 7:
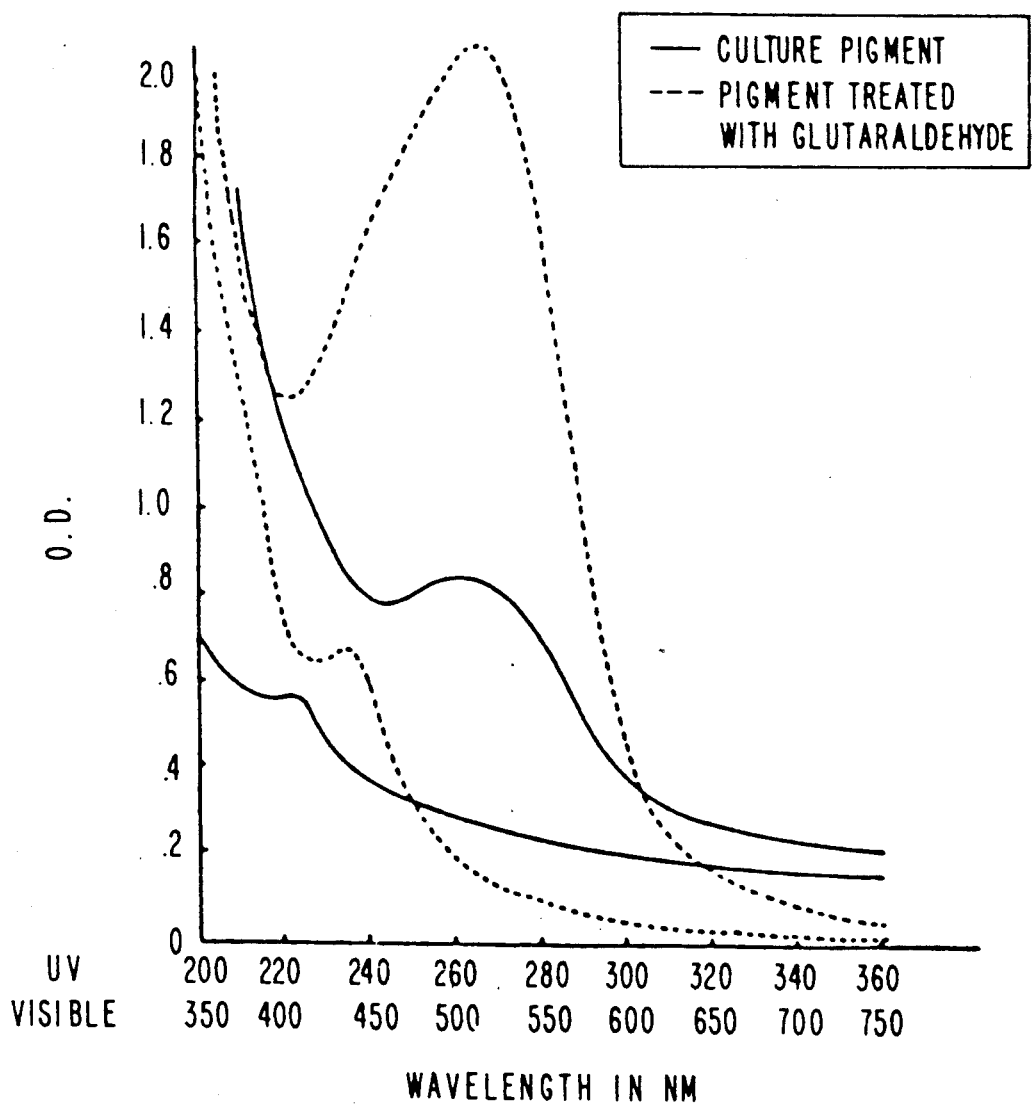
FIG. 7 is a graphic illustration depicting the absorbance spectra of culture pigment and a glutaraldehyde-treated pigment.
Figure 8:
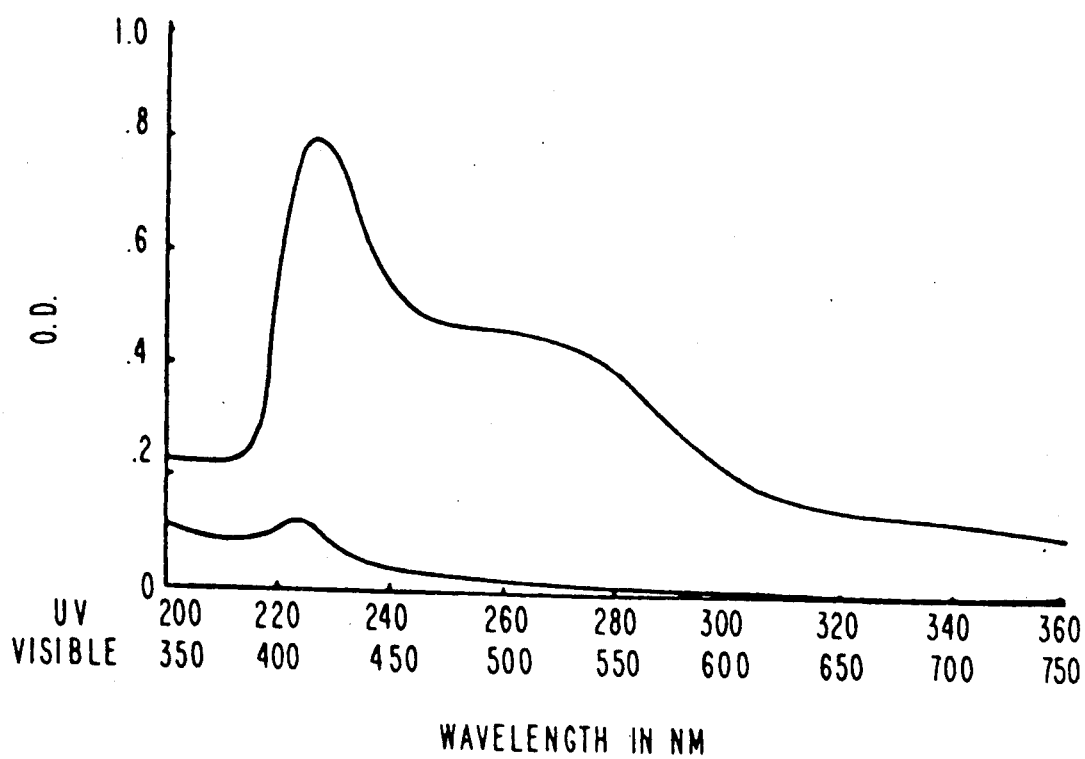
FIG. 8 is a graphic illustration depicting the absorbance spectrum of a pigment fraction purified on a Sephadex G-75 column.
Figure 9:
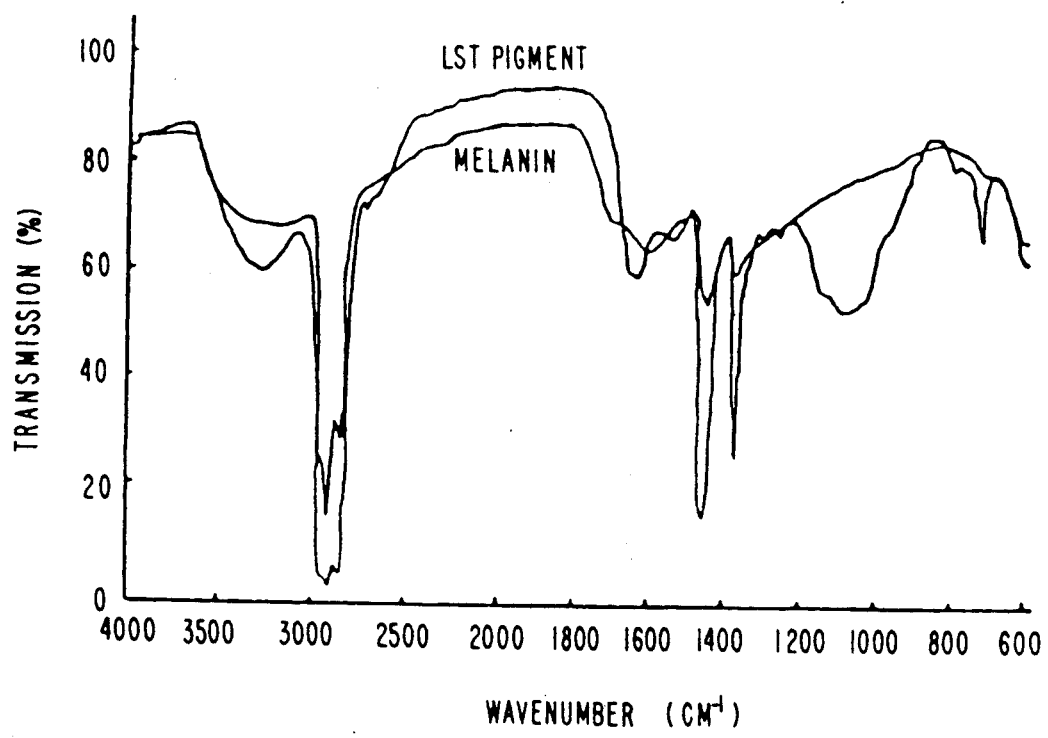
FIG. 9 is an IR spectrum pattern of melanin and LST pigment.

The absorption spectra of the experimental LST pigment was compared with spectra of commercial melanin, which had peaks at 225 and 273 nm, and with L-DOPA, which had peaks at 233, 282 and 512 nm. The LST product absorbance maxima were deemed to sufficiently match those of the commercial preparation to conclude that LST did indeed produce a melanin. Further purified LST pigments tended to support that hypothesis. Pigment fractions obtained from Sephadex G-75 and G-150 columns yielded absorbance maxima at 226, 263 and 407 nm (FIG. 4). A peak in the visible region was not detected in the commercial pigment preparation, possibly due to the consequence of the low solubility of melanin (viz., a particle-free suspension was not sufficiently concentrated).

Shellfish Attachment

Three spat setting tanks were filled with seawater (25° C.) and presetting (eyed) oyster larvae. Acid cleaned (1N HCl, 24 hrs) and sterilized glass slides were immersed in Set Tank 1. Glass slides, categorized and treated as follows, were placed in Set Tank 2:
1. Pigmented LST: Slides were immersed for 24 hrs in a stationary phase culture of LST, grown in Marine Broth at 25° C.
2. UV irradiated LST: Slides were immersed for 24 hrs in a late stationary phase culture of LST, grown in Marine Broth at 25° C. The slides were then exposed to lethal doses of UV radiation.
3. Marine Broth control: Slides were immersed in uninoculated media for 24 hrs.

In Set Tank 3, plates and glass slides were treated in the following manner:
1. 10 mg DOPA per 10 ml 2% noble agar.
2. 50 mg DOPA per 10 ml 2% noble agar.
3. 100 mg DOPA per 10 ml 2% noble agar.
4. 10 mg commercial melanin per 10 ml 2% noble agar.
5. 20 mg commercial melanin per 10 ml 2% noble agar.
6. 10 ml noble agar (control).
7. Culture pigment: An LST culture in the late stationary phase of growth (Marine Broth at 25° C.) was centrifuged (2500×g, 10 min) and the supernatant filtered through 1.2 um Millipore filters to further remove cells. Slides were immersed in the cell-free filtrate for 24 hrs.

After 24 hrs in the setting tanks, all slides and plates were removed and the attached spat were counted using a stereoscope (10X; Baush and Lomb).

One caveat must be noted. The pigment coated slides and all of the Agar plates were placed in one tank. The DOPA dissolved in the water (high solubility, large water volume), autooxidized, and a thin deposit coated all the plates, slides and tank surfaces. Thus, the attached spat population may have been enhanced.

Data such as those reported in Tables 7 and 8, together with other evidence, supports the notion that LST pigment promotes shellfish attachment. Slides coated with pigmented LST attracted more than 5 times the oyster spat than the clean and control slides (Tables 7 and 8). Interestingly, slides coated with UV-irradiated LST attracted slightly less spat than the controls.

The data involving Agar plate imbedded with the test substance and glass slides coated with culture pigment are to be interpreted much more cautiously, since the DOPA diffused out of the Agar, autooxidized, infiltrated the tank and interfered with experimental gradients. Nevertheless, melanin Agar plates also attracted more spat than the control plates, while DOPA Agar plates attracted 2-5 times less larvae than the controls. The number of spat (attached oysters) was inversely proportional to the concentration of DOPA in the Agar, suggesting that at high concentrations, DOPA may have a repelling or toxic effect on the shellfish. The pigment coated slides, placed in the same tank with the Agar plates, attracted almost 10 times the number of spat attached to the control slides.

Isolation and Purification of Acid Polysaccharide Exopolymer

LST, DIF and HYP in 3% brain heart infusion agar (3 BHI) secretes an acid polysaccharide exopolymer amounting to approximately 500% of the weight of the bacterium in 48 hrs at 25° C. This exopolymer is isolated as follows:
1. 3 BHI in large petri plates is inoculated with 1 ml of $10^8$ LST, DIF or HYP grown as described above.
2. The culture is incubated for 2 days.
3. The acid polysaccharide exopolymer is solubilized in an acetone-alcohol or isopropanol solution.
4. The exopolymer is precipitated at the water-solvent interface.
5. For purer preparations, treatments with DNAase and protease were also employed.

Larval Induction

LST, DIF and HYP are grown in a conventional growth vessel fermentator (NBC CMF 128S) filled to 15 liters. A series of these vessels accommodates coated clutch or slides to induce the metamorphosis of 10,000 spat.

The bacterial cells are grown as indicated above and slides are immersed in the growth vessel. The bacteria affix to the slides via the adhesive exopolymer they produce.

The bacteria-coated surfaces are removed from the fermentor and placed at the bottom of a larval set tank. Larvae are exposed to the bacteria in filtered, slow moving water. The steady state setup can remain active for months. The activated clutch or slides are restored each new setting season. Salinities range from 1.8 to 2.5%.

The oysters are fed *Isochrysis galbana* and *Monochrysis lutheri* at a rate of approximately $2 \times 10^5$ cells/ml of culture per day.

Thus, while the invention has been described with reference to certain preferred embodiments, those skilled in the art will realize that changes and modifications may be made thereto without departing from the full and intended scope of the appended claims.

EXAMPLE II

EXTRACTION OF PAVE (POLYSACCHARIDE ADHESIVE VISCOUS EXOPOLYMER)

Media

Alteromonas strains were maintained on marine aoar 2216 (MA; Difco). Five different media were tested for their ability to maximize PAVE production by *A. colwelliana:* Brain hear infusion broth (BHI; Difco) ammended with 2.5% NaCl; Marine broth 2216 (MB; Difco); Marine broth plus 1.0% glucose; Marine broth plus 1.0% casein hydrolysate (CH; Gibco and 1.0% CH plus marine salts [30].

Extraction of PAVE

A variety of methods were tested for the extraction of *A. colwelliana* polysaccharide. In the course of these experiments, it was noted that PAVE was tightly bound to the cells, but that it could be separated by treatment with urea or EDTA. Centrifugation was found to be the most effective method to separate the cells from the polysaccharide exopolymer. Several solvents were tested for efficient precipitation of PAVE including methanol, ethanol and isopropanol. The following procedure was found to produce the greatest yield and most consistent product.

*A. colwelliana* LST strain D was grown to late logsrithnic-early stationary phase of growth. EDTA was added to the broth (3.72 g/l) which was stirred for 15 minutes. The cells were removed (Sorvall RC-5B Centrifuge) at 8,000 rpm for 8 minutes. PAVE was precipitated by the addition of 4 volumes of isopropanol (25° C). A curved glass rod was used to mix the solution and to remove any spoolable precipitate. The remaining precipitate was collected at 10,000 rpm after 15 minutes, dried with a stream of air (until the odor of isopropanol could no longer be detected), resuspended in distilled water and lyophilized. The powdered PAVE (purified PAVE) was stored at −20° C. for further analysis. A sample was obtained at each step in the extraction procedure for carbohydrate and protein analysis.

Alternatively, mucoid exopolymers from selected isolates of marine bacteria were scraped from BHI +2% NaCl agar surfaces diluted 1:10 or 1:100 in acetone (crude PAVE). Samples were designated (see Table 11) according to the strain from which they were obtained.

Carbohydrate Analysis

Several methods were tested for the accurate determination of PAVE yields. These methods were: the phenol-sulfuric acid assay; cysteine-sulfuric acid assay; carbazole-sulfuric acid assay; and the anthrone assay.

Glucose, xanthan gum, alginic acid and glucuronic acid were used as standards and samples. Bovine serum albumin and a marine broth cultures were also included as samples.

Viscosity

A Brookfield Digital Viscometer, model LTVDCP was used to determine the viscosity of 1% solutions of the lyophilized PAVEs. The sample sup was covered with approximately 1.1 ml of the solution. Viscosity readings were taken every 30 minutes until the viscosity was constant for 60 minutes. The viscometer was standardized with Brookfield fluid #10 standard which has a viscosity of 9.3 cP at 25° C.

Molecular Weight Determinations

Sepharose gel 6B (Pharmacia; 50×1.3 cm I.D.) was used to fractionate PAVE according to molecular weight. Chromatographic separations were carried out at 4 C with PBS containing 0.02% sodium azide as eluent (flow rate of 5 ml/hour; 2232 Microperpex S peristaltic pump; 2238 Uvicord S II ultraviolet detector; 2210 2-channel recorder). Five ml fractions were collected (LKB 2212 Helirac). One ml of each fraction was also tested by the phenol-sulfuric acid assay to detect carbohydrates which do not absorb at 280 nm. The void volume was determined with 2,000,000 daltons molecular weight blue dextran (Pharmacia). The molecular weight standards were 500,000 daltons and 10,000 daltons dextran or ferritin (440,000 daltons) and ribonuclease A (13,700 daltons: Pharmacia).

Survey for Adhesive Properties

Adhesiveness was empirically determined on glass microscope slides which had been cleaned with 2M sulfuric acid and acetone. The procedures were: A. colwelliana LST purified PAVE (40 ul of 1.0% solutions) preparations were applied to adhere two 2.5 cm by 2.5 cm surfaces. For other bacterial PAVEs, the mucoid exopolymers scraped from agar plates and diluted in acetone were spread over 2.5 cm by 2.5 cm portion of one slide and clamped to another slide. Unless otherwise stated, the slides were allowed to cure for 1 to 7 days. Torque force was exerted near the end of the assembly, approximately 5 cm from midjoint. The torque force required to break the bond was measured.

Determination of Integral and Contaminating Polymers in PAVE

Protein concentrations were determined by the Bradford assay. Standard Laemmli SDS-PAGE disc gels were used to characterize contaminating or integral protein. Melanins and other products of tyrosinase activity were detected by visual inspection of respective pigments.

Contaminating DNA was detected by electrophoresis of the PAVE fractions on a 1% agarose gel using 10 ul of the fractions mixed with 2.5 ul of loading buffer (0.25% bromophenol blue; 40.0% sucrose). TAE (0.04 M Tris-acetate, 0.001 M EDTA) buffer plus ethidium bromide (0.5 ug/ml final concentration) was used to pour and run the gel (1.5 hrs). DNA bands were visualized under UV light.

The presence of DNA was confirmed by treating the PAVE fractions with DNAase. To 100-400 ul of PAVE: 10 ul stock DNAase (1 mg/ml) and 50 ul 10X buffer (0.5 M tris, 0.05 M MgCl$_2$, pH −7.8) were added. The volume was adjusted to 500 ul with distilled water. The reaction mixture was placed at 37 C for 1-2 hours.

A sample of the treated PAVe was run on a 1.0% agarose gel with an untreated control to confirm the disappearance of the putative DNA.

TABLE 1

Some biochemical and physical characteristics of LST

| Test | Reaction |
|---|---|
| Gram stain | gram neg |
| Cell shape | rod |
| Spores | − |
| Motility | + |
| Catalase | + |
| Lysine decarboxylase | + |
| Ornithine decarboxylase | − |
| Sucrose fermentation | − |
| Mannose fermentation | − |
| Arabinose fermentation | − |
| Growth in 2.5% NaCl | + |
| Growth in 5.0% NaCl | + |
| Growth in 7.5% NaCl | + |

TABLE 2

Contributions of aspartic acid (asp), glutamic acid (Glu), methionine (Met) and serine (Ser) to the growth of LST[a]

| Amino Acids | Growth[b] |
|---|---|
| Asp Glu Met | +++ |
| Asp Met Ser | +++ |
| Glu Met Ser | +++ |
| Asp Ser | +++ |
| Ser Met | − |
| Asp Glu | +++ |
| Asp Met | + |
| Ser Glu | ++ |
| Glu Met | ++ |

[a]Inorganic salts solution (Appendix I) was supplemented with each of the amino acids listed in the concentrations used in the AGMS medium.
[b]+++, ~7 hr generation time; ++, ~10 hr generation time; +, ~13 hr generation time; −, no growth.

TABLE 3

Adenyl nucleotide pool in a hypo-pigment producing varient of LST cultivated in batch culture[a]

| Growth Phase | Viable Count (cfu/ml) | Morphology | AEC[b] | pM ATP/Cell | ug/Cell[c] |
|---|---|---|---|---|---|
| Log | $4.5 \times 10^7$ | Short Rods | 0.86 | $1.19 \times 10^{-7}$ | $6.56 \times 10^{-11}$ |
| Stationary | $2.9 \times 10^9$ | Rods | 0.80 | $1.73 \times 10^{-9}$ | $9.53 \times 10^{-13}$ |
| Stationary-Decline | $2.7 \times 10^7$ | Long Spirals | 0.72 | $1.61 \times 10^{-9}$ | $8.86 \times 10^{-13}$ |

[a]Cells were removed from a batch culture of LST during log phase, stationary phase and during the stationary-decline transition and were then frozen (−70° C.). Adenyl nucleotides were extracted in boiling tris. The samples were then assayed for ATP, ADP and AMP and adenylate energy charge (AEC) was calculated.
[b]Calculations were based on known internal standards that revealed recovery and counting efficiencies of 72.4% for ATP, 41.6% for ADP, 38.0% for AMP.
[c]ug ATP per cell was calculated by multiplying pM/cell by $10^{-6}$ and by ATP mol. wt.

TABLE 4

Solubility of LST excreted pigment (in spent medium) in seven solvents

| Solvent | Solubility[a] | Precipitate[b] | Absorbance[c] Maxima |
|---|---|---|---|
| H₂O, pH 3 | S | +(24 h) | 264, 401 |
| H₂O, pH 9 | S | − | 264, 407 |
| Acetone | I | +(30 s) | none |
| Ethanol | SS | +(30 s) | 254, 375 |
| Methanol | SS | +(30 s) | 246, 264, 400 |
| Ethylene dichloride | I | − | 233, 264, 400 |
| Chloroform | I | − | 243, 276 |
| Cyclohexane | I | − | 203, 222 |

[a]S-relatively soluble; SS-slightly soluble; I-insoluble
[b]+ Precipitate formed (time at which formed)
− No precipitate formed
[c]Absorbance maxima of pigment-solvent mixtures vs. solvent references

TABLE 5

Spectral absorbances of pigments extracted from LST

| Sample | Dilution | Absorbance Maxima[a] | Optical densities at Abs. Maxima |
|---|---|---|---|
| Marine Broth | 1:8 | 260 | 1.10 |
| Supernatant | 1:4 | 407 | 0.50 |
| LST-Associated Pigment | 1:16 | 264 | 0.36 |
|  | 1:4 | 407 | 0.33 |
| LST-Associated and Soluble Pigment | 1:64 | 260 | 0.38 |
|  | 1:4 | 407 | 0.25 |
| Red-Black Pigment Treated w/Glut[b] | 1:64 | 237 | 1.08 |
|  | 1:1000 | 293 | 0.24 |
| Dark Orange Pigment | 1:64 | 234 | 1.34 |
| -Glut- | 1:64 | 272 | 0.58 |
|  | 1:4 | 436 | 0.60 |
| Yellow Pigment | 1:64 | 232 | 1.17 |
| -Glut- | 1:64 | 274 | 0.38 |
|  | 1:4 | 434 | 0.22 |
| Orange Pigment | 1:64 | 265 | 2.00 |
| -Glut- | 1:2 | 436 | 0.34 |
| Crude Pigment Extract[c] | 1:4 | 256 | 1.16 |
|  | none | 405 | 0.11 |
| Commercial Melanin 0.25 mg/ml | 1:4 | 225 | 0.43 |
|  | 1:4 | 273 | 0.31 |
| Commercial L-DOPA 1.0 mg/ml | 1:4 | 233 | 3.00 |
|  | 1:4 | 282 | 2.90 |
|  | none | 512 | 0.37 |

[a]There were 2-3 maxima for each sample. See text and FIG. 3 legend for further detail.
[b]Gluteraldehyde, an SEM fixative.
[c]Crude pigment extract was obtained by redissolving crude pigment crystals in distilled water to solubility limit (exact concentration unknown).

TABLE 6

Toxicity of Ethyl Methane Sulfonate (EMS) to LST[a]

| EMS Conc. | Direct Growth[b] | | Growth after Holding[c] | |
|---|---|---|---|---|
| ug/ml | MA | AG | MA | AG |
| 10 | $3.7 \times 10^6$ | No Data[d] | $1.4 \times 10^9$ | $1.5 \times 10^7$ |
| 15 | $3.7 \times 10^6$ | No Data[d] | No Data | No Data |
| 20 | $7.0 \times 10^7$ | No Data[d] | $6.6 \times 10^9$ | $6.5 \times 10^7$ |
| 25 | $6.9 \times 10^7$ | No Data[d] | $3.2 \times 10^9$ | $2.1 \times 10^7$ |
| 30 | $7.1 \times 10^7$ | No Data[d] | $1.3 \times 10^9$ | $1.4 \times 10^7$ |
| original culture | $6.7 \times 10^9$ | $3.8 \times 10^9$ | — | — |

[a]LST was exposed to EMS concentrations for 1 hr.
[b]Mutagenized suspensions were spread on plates immediately after exposure to EMS.
[c]Aliquots of mutagenized suspensions were "held" in AG Broth for 2-5 days, after which they were spread on Marine (MA) and AG agars.
[d]The dilutions plated did not yield any colonies.

TABLE 7

Density of *Crassostrea virginica* larvae attached to glass and agar surfaces

| Slide or Agar Plate Preparation[a] | Attached Spat Density[b] |
|---|---|
| Clean and Marine Broth Control Slides (I) | 0.11/in$^2$ (16) |
| Pigmented LST (II) | 0.58/in$^2$ (16) |
| UV Irradiated LST (II) | 0.07/in$^2$ (16) |
| Culture Pigment (III) | 1.00/in$^2$ (10) |
| 10 mg DOPA/10 ml agar (III) | 1.03/in$^2$ (2) |
| 50 mg DOPA/10 ml agar (III) | 0.42/in$^2$ (2) |
| 100 mg DOPA/10 ml agar (III) | 0.42/in$^2$ (2) |
| 10 mg melanin/10 ml agar (III) | 2.22/in$^2$ (2) |
| 20 mg melanin/10 ml agar (III) | 2.55/in$^2$ (2) |
| Agar Control/10 ml agar (III) | 2.12/in$^2$ (2) |

[a]Number in parentheses designates the spat tank used.
[b]Number in parentheses designates the number of samples taken.

TABLE 8

Attraction of *Crassostrea virginica* larvae by the bacteria LST, a melanin synthesizing species

| Sample Type[a] | Sample No.[b] | Mean No. Spat at 24 h[c] | 95% Confidence Interval[d] |
|---|---|---|---|
| Control[e] | 16 | 3.8 ± 1 | 1 < > 7 |
| Prefouled[f] | 27 | 24.8 ± 7 | 12 < > 38* |
| *Hyphomonas neptunium*[g] | 14 | 5.0 ± 2 | 2 < > 8 |
| LST[g] | 16 | 17.5 ± 3 | 12 < > 23* |
| Pigment from LST[g] | 10 | 30.0 ± 14 | 2 < > 58 |
| UV Killed LST[g] | 16 | 1.8 ± 1 | 0 < > 4 |
| Control[e] | 5 | 2.4 ± 1 | 2 < > 3 |
| LST[g] | 14 | 9.7 ± 1 | 7 < > 12* |
| LST Hypopigment producer[g] | 8 | 2.0 ± 1 | 1 < > 4 |

[a]First 6 samples were run on 1/81 and last 3 samples were run on 7/81 at the oyster mariculture unit in Lewes, Delaware.
[b]Chemically cleaned and sterilized 3 in X1 microscope slides.
[c]Larval settlement and/or attachment per slide X10. Standard error also shown.
[d]Asterisk denotes significant deviation from control samples.
[e]Placed in Marine medium for 24 hrs prior to immersion in oyster tank.
[f]Slides placed in mariculture holding tank (~10$^5$ viable bacteria/ml) prior to immersion in oyster tank.
[g]Slides were coated with sample type prior to immersion in oyster tank.

TABLE 9

LST properties of pigment compared with pigments identified as melanin of other microorganisms

| PROPERTIES | *Aeromonas*[a] *liquefaciens* | *Vibrio*[b] *cholerae* | *Aspergillus*[c] *nidulans* | LST[d] |
|---|---|---|---|---|
| Color | Brown-Black | Brown | Black | Brown |
| Solubility in H$_2$O at pH 7 | I | ND | ND | SS |
| Solubility in 0.1N NaOH | S | S | S | S |
| Blackberg-Wanger Precipitation | PPT | PPT | ND | PPT |
| FeCl$_3$ Precipitation | PPT | PPT | PPT | PPT |
| Acid Precipitation | PPT | PPT | PPT | PPT |
| Reduction (Glutathione) | + | + | + | + |
| Reoxidation | + | ND | + | + |
| Absorption Peaks | Diffuse | 345,480 | 480,535 | 264,407 |
| H$_2$O Bleaching | ND | + | + | + |
| Molecular Weight | ND | ND | 2,000,000 | 120,000 |
|  |  |  | 350,000 | 52,000 |
|  |  |  | 29,000 | 12,000 |

I-insoluble; S-soluble; ND-no data; PPT-precipitated; +-positive
[a]Aurstad and Dahle 1972
[b]Ivins and Holmes 1980
[c]Bull 1970
[d]Present study

TABLE 10

Physical Characteristics of PAVE Extracted by Isopropanol From LST-D Grown to Stationary Phase in Selected Broths

| Medium[a] | GMS/L[b] | uMAX[c] | C/P[d] | VISC[e] |
|---|---|---|---|---|
| BHI | 11.2 | 490 | 1.1 | 6.6 |
| MB + CH | 9.1 | 487 | 1.3 | 3.7 |
| CH | 8.6 | 484 | 0.9 | 2.3 |
| MB + GLU | 7.1 | 490 | 14.4 | 0.9 |
| MB | 5.0 | 490 | 2.8 | 1.7 |

[a]Brain Heart Infusion (BHI); Marine Broth 2216 (MB); MB + 1.0% (w/v) Glucose (MB + GLU); MB + Casein Hydrolysate (MB + CH); Casein Hydrolysate (CH).
[b]Dry weight of purified PAVE/liter culture.
[c]Wavelength of maximum absorption of Phenol Sulfuric Acid assay (PSA).
[d]Carbohydrate/protein as determined by PSA and Bradford (1976) assays, respectively.
[e]Viscosity (centipoises) - measured with Brookfield Digital Viscometer (Model LVDTCP, CP-42 spindle, motor setting of 12) of 1% (w/v) aqueous solution of purified, lyophilized PAVE.

TABLE 11

Relative Adhesive Strength of Crude PAVE Preparations from Marine Bacteria[a]

| Sample | Solvent | Days Cured | Torque Force (gm cm)[b] |
|---|---|---|---|
| MPF-1 | Acetone | 50 | 1180 [140] |
| RAM-1 | Acetone | 50 | 2215 [1085] |
|  | Acetone | 6 | 3950 [1260] |
|  | Water | 6 | 1430 [625] |
|  | Salt Water (1%) | 6 | 950 [465] |
| KAN-1 | Acetone | 6 | 2690 [530] |
|  | Water | 6 | 4240 [260] |
|  | Salt Water (1%) | 6 | 3310 [670] |
| TAC-1 | Acetone | 6 | 4355 [535] |
|  | Water | 6 | 2415 [40] |
|  | Salt Water (1%) | 6 | 1480 [110] |
| TAC-2 | Acetone | 6 | 1935 [40] |
|  | Water | 6 | 1195 [295] |
| Water | — | — | 2 |

[a]PAVE harvested from PAVE-enriched surface growth and diluted 1:10 into solvent. Glaxx (2.5 × 2.5 cm) pressure joined.
[b]Torque applied 5 cm from mid-joint. Bracketed numbers are Std. Dev.

What is claimed is:

1. A method for inducing the settlement and metamorphosis of *Crassostrea viginica* larvae comprising exposing said larvae in an aqueous medium to melanin-synthesizing bacteria of the genus *Alteromonas* for a time and under conditions sufficient to induce the settlement and metamorphosis of said oyster larvae.

2. The method of claim 1 wherein the species of said melanin-,synthesizing bacteria is *A. colwelliana*.

3. A method for inducing the settlement and metamorphosis of *Crassostrea virginica* larvae comprising exposing said larvae in aqueous medium to the metabolic products of a melanin-synthesizing marine bacteria of the genus Alteromonas for a time and under conditions sufficient to induce the settlement and metamorphosis of said larvae, said metabolic products selected from the group consisting essentially of melanin, dihydroxyphenylalanine, pheomelanin, tyrosine, tyrosinase, tyrosinase related enzymes, NH3, the catecholamine products of tyrosinase having a molecular weight of less than about 350 daltons, PAVE, trihydroxyphenylalanine and mixtures thereof.

4. The method of claim 3 wherein the species of said melanin-synthesizing bacteria is *A. colwelliana*.

5. The method of claims 1 wherein the bacteria are provided with a suitable surface material to effect affixment of said bacteria.

6. The method of claim 5 wherein the surface material is clutch, glass, plastic or aluminum.

7. The method of claims 1 or 3 wherein the bacteria have the identifying characteristics of ATCC number 33887 and mutants of said bacteria.

8. The method of claims 1 or 3 wherein the bacteria have the identifying characteristics of ATCC number 33888 and mutants of said bacteria.

9. The method of claims 1 or 3 wherein the bacteria have the identifying characteristics of ATCC number 39565 and mutants, of said bacteria.

10. The method of claims 1 or 3 wherein the bacteria have the identifying characteristics of ATCC number 27126 and mutants of said bacteria.

11. The method of claims 1 or 3 wherein the bacteria have the identifying characteristics of ATCC number 23327 and mutants of said bacteria.

12. The method of claims 1 or 3 wherein the bacteria have the identifying characteristics of ATCC number 53761 and mutants of said bacteria.

13. A method for inducing the settlement and metamorphosis of *Crassostrea virginica* larvae comprising exposing said larvae in aqueous medium to ammonia ($NH_3$) in concentrations and under conditions sufficient to induce the settlement and metamorphosis of said bacteria.

14. The method of claim 13 wherein the concentration of said ammonia is about $2 \times 10^{-3}$M to about $2 \times 10^{-2}$M at a pH of about 8.0.

15. The method of claim 14 wherein said concentration is about $8 \times 10^{-3}$M at a pH of about 8.0.

* * * * *

UNITED STATES PATENT AND TRADEMARK OFFICE
CERTIFICATE OF CORRECTION

PATENT NO. : 5,047,344
DATED : September 10, 1991
INVENTOR(S) : Ronald Weiner, et al.

It is certified that error appears in the above-indentified patent and that said Letters Patent is hereby corrected as shown below:

On the Title Page, Section [73]: "Techniques" should read --Technologies--

In the Abstract, line 12: after "invention" delete "." and insert --,--

Column 4, line 59: delete "("

Column 5, lines 3-4: delete "are variants"

Column 5, line 29: delete "/"

Column 6, line 9: delete "["

Column 6, line 51: "NH" should read --$NH_3$--

Column 6, line 65: "able-" should read --able--

Column 9, line 53: "Morphologqy" should read --Morphology--

Column 9, line 54: "cyclc" should read --cycle--

Column 12, line 24: delete "-"

Column 13, line 54: after "agar" insert --.--

Column 15, line 67: "sup" should read --cup--

Column 18, line 20: delete "0.11" and insert --0.11-- under --$Extract^c$--

UNITED STATES PATENT AND TRADEMARK OFFICE
CERTIFICATE OF CORRECTION

PATENT NO. : 5,047,344
DATED : September 10, 1991
INVENTOR(S) : Ronald Weiner, et al.

It is certified that error appears in the above-indentified patent and that said Letters Patent is hereby corrected as shown below:

Column 18, line 58: "15   3.7" should read --15   1.3--

Column 20, line 58, Claim 3: "NH3" should read --$NH_3$--

Column 20, line 64, Claim 5: "claims" should read --claim--

Signed and Sealed this

Seventh Day of February, 1995

Attest:

BRUCE LEHMAN

*Attesting Officer*     *Commissioner of Patents and Trademarks*